(12) United States Patent
Abolin et al.

(10) Patent No.: US 8,501,994 B2
(45) Date of Patent: Aug. 6, 2013

(54) ACETAMIDE STEREOISOMER

(75) Inventors: Craig R. Abolin, Boylston, MA (US);
H. Scott Wilkinson, Westborough, MA
(US); Paul McGlynn, Northborough,
MA (US); William K. McVicar,
Sudbury, MA (US)

(73) Assignee: Sunovion Pharmaceuticals Inc.,
Marlborough, MA (US)

( * ) Notice: Subject to any disclaimer, the term of this
patent is extended or adjusted under 35
U.S.C. 154(b) by 882 days.

(21) Appl. No.: 12/196,520

(22) Filed: Aug. 22, 2008

(65) Prior Publication Data
US 2009/0060922 A1 Mar. 5, 2009

Related U.S. Application Data

(60) Provisional application No. 60/966,438, filed on Aug. 28, 2007.

(51) Int. Cl.
*C07C 233/05* (2006.01)
*A61K 31/16* (2006.01)

(52) U.S. Cl.
USPC ........... 564/221; 564/216; 564/217; 564/223; 514/630

(58) Field of Classification Search
USPC ................. 564/216, 217, 221, 223; 514/230, 514/630
See application file for complete search history.

(56) References Cited

U.S. PATENT DOCUMENTS

| | | | |
|---|---|---|---|
| 3,994,974 | A | 11/1976 | Murakami et al. |
| 6,040,344 | A | 3/2000 | Gao et al. |
| 6,268,533 | B1 | 7/2001 | Gao et al. |
| 6,303,145 | B2 | 10/2001 | Jerussi et al. |
| 6,472,563 | B1 | 10/2002 | Tanoury et al. |
| 6,720,453 | B2 | 4/2004 | Tanoury et al. |
| 7,145,036 | B2 | 12/2006 | Tanoury et al. |
| 7,342,132 | B2 | 3/2008 | Tanoury et al. |
| 7,479,572 | B2 | 1/2009 | Tanoury et al. |

FOREIGN PATENT DOCUMENTS

| | | |
|---|---|---|
| DE | 2305092 A1 | 8/1973 |
| ES | 2005492 | 3/1989 |
| ES | 2031407 | 12/1992 |
| JP | 56-115751 * | 9/1981 |
| WO | 97/25311 A1 | 7/1997 |
| WO | 98/21175 A1 | 5/1998 |

OTHER PUBLICATIONS

RN 80084-90-8, 1981.*
Chemical Abstracts Service; XP-002513562, "3-Acylamino-4-hydroxy-.alpha.-(aralkylaminomethyl)benzyl alcohols," 6373 (1982).
Akapo et al.; "Validation of a RP-HPLC method for the assay of formoterol and its related substances in formoterol fumarate dihydrate drug substance." *Journal of Pharmaceutical and Biomedical Analysis*; vol. 33, pp. 935-945. (2003). XP-002513561.
International Search Report and Written Opinion—for International Application No. PCT/US2008/074653.
Hett et al.; Large Scale Synthesis of Enantio- and Diastereomerically Pure (R,R)-Formoterol. *Organic Process Research & Development*. 2, 96-99, (1998).
Hett et al.; Conformation Toolbox of Oxazaborolidine Catalysts in the Enantioselective Reduction of α-Bromo-Ketone for the Synthesis of (R,R)-Formoterol. *Tetrahedron Letters*. 39, 1705-1708, (1998).
Hett et al.; Enantio-and Diastereoselective Synthesis of all Four Stereoisomers of Formoterol. *Tetrahedron Letters*. XP-002057058. vol. 18, No. 7 pp. 1125-1128, (1997).
Murase et al.; New β-Adrenoreceptor Stimulants. Studies on 3-Acylamino-4-hydroxy-α-(N-substituted aminomethyl)benzyl Alcohols[1]). *Chem Pharm. Bull*.vol. 25 (6) 1368-1377, (1977).
Kurihara et al.; (-)-Formoterol, a Selective $β_2$—Adrenoreceptor Agonist. *Acta Cryst*. C53, 1887-1889, (1997).

* cited by examiner

*Primary Examiner* — Shailendra Kumar
(74) *Attorney, Agent, or Firm* — Heslin Rothenberg Farley & Mesiti PC

(57) ABSTRACT

The compound of formula (I)

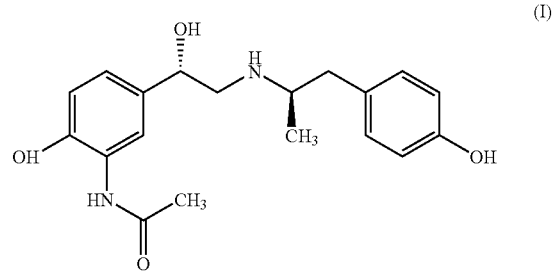

(I)

is a water-stable, long acting $β_2$-selective adrenoceptor agonist useful as a bronchodilator in the treatment of bronchoconstriction associated with reversible obstructive airways diseases and the like.

15 Claims, No Drawings

ACETAMIDE STEREOISOMER

CROSS REFERENCE TO RELATED APPLICATION

This application claims priority to U.S. Provisional Application No. 60/966,438 filed Aug. 28, 2007, the entire disclosure of which is herein incorporated by reference.

FIELD OF THE INVENTION

The present invention relates to a novel acetamide stereoisomer, to a process for preparing the acetamide stereoisomer, to a pharmaceutical composition comprising the acetamide stereoisomer and to the use of the acetamide stereoisomer in therapy, in particular in the treatment of bronchoconstriction associated with reversible obstructive airways diseases including but not limited to asthma, cystic fibrosis and chronic obstructive pulmonary disease, including chronic bronchitis and emphysema.

BACKGROUND OF THE INVENTION

Patients suffering from bronchoconstriction associated with reversible obstructive airways diseases are generally treated using a bronchodilator, to relax the bronchial smooth muscle.

Bronchodilators in use today generally fall into two classes, the $\beta_2$-selective adrenoceptor agonists, such as albuterol (salbutamol), salmeterol and formoterol, and the muscarinic receptor antagonists, such as ipratropium and tiatropium.

$\beta_2$-Selective adrenoceptor agonists may cause adverse effects, and these may in part be due to activation of the $\beta_1$-adrenoceptor. The selectivity of an agonist for the $\beta_2$-adrenoceptor receptor is therefore very important, because it limits the dose that can be given and so affects the magnitude of bronchodilations and the frequency of dosing.

A long duration of action is important to patients, not only to minimize the time spent taking the drug, but also to avoid having to take the drug during inconvenient times, for example at work, school or during the night. Some of the more recent $\beta_2$-selective adrenoceptor agonists, in particular salmeterol and formoterol, have a long duration of action, typically about 12 hours. Formoterol has a particular advantage that it also has a fast onset of action. However, formoterol is extremely potent, which makes it very difficult to formulate, especially for administration using a metered dose inhaler in a manner that results in uniform drug delivery via aerosol dose after dose (i.e., dose content uniformity). Furthermore, it is unstable in aqueous solution, which means that solutions for administration using a nebuliser have to be kept refrigerated for a majority of their post-manufacture shelf life.

Formoterol is one of a group of α-aminomethylbenzyl alcohol derivatives for which patent applications were filed during the early nineteen seventies, for example GB 1 415 256. Perhaps because of the difficulties associated with formulating the compound, it took a long time to be commercialized. The compound contains two chiral centers, and hence is capable of existing and being isolated in four stereoisomeric forms. The compound was firstly commercialized as a racemic mixture of the active (R,R)- and inactive (S,S)-isomers, in a dry powder formulation, then more recently as the active (R,R)-isomer in a nebuliser solution. It is also known, for example from U.S. Pat. No. 6,303,145, that the (S,R) isomer of formoterol is active. However, like the (R,R)-isomer, this compound is unstable at ambient temperature in aqueous solution and hence nebuliser solutions would need to be stored refrigerated.

SUMMARY OF THE INVENTION

Surprisingly, it has now been found that by replacing the methoxy group in (S,R)-formoterol with a hydroxy group, and the formyl hydrogen atom with a methyl group, an isomer having a particularly attractive combination of properties has been obtained.

According to one aspect, therefore, the present invention provides a compound of formula (I)

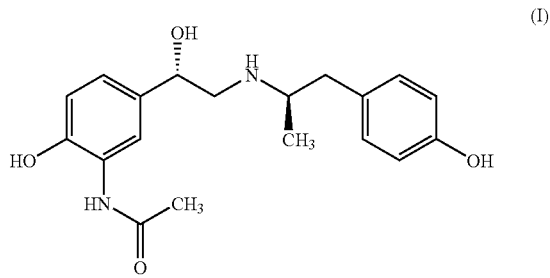 [SMILES: CC(=O)Nc1cc([C@H](O)CN[C@H](C)Cc2ccc(O)cc2)ccc1O]

or a pharmaceutically acceptable salt thereof.

The compound of formula (I) may also be referred to by the chemical name N-[2-hydroxy-5-[(1S)-1-hydroxy-2-[[(1R)-2-(4-hydroxyphenyl)-1-methylethyl]amino]ethyl]phenyl]acetamide.

The isomer of formula (I) has been found to possess particularly advantageous properties. In particular, it possesses good, but not very high affinity for the $\beta_2$-adrenoceptor, high selectivity for the $\beta_2$- over the $\beta_1$-adrenoceptor, a long duration of action and good stability in aqueous solution at ambient temperature.

DETAILED DESCRIPTION OF THE INVENTION

It will be appreciated that the compound provided by the present invention is an isomer. This isomer may exist and be isolated in enantiomerically pure form, or in admixture with one or more of its other isomers. The present invention provides the isomer in any mixture of isomers other than a racemic mixture, which is described in GB 1,415,256. In certain embodiments, the isomer is substantially free of the (R,R)-enantiomer, which can exhibit a different potency, resulting in significant variations in the potency of admixtures. It may exist as a 1:1 diastereomeric mixture with the (R,S)-isomer, but is most preferably enantiomerically pure (i.e. substantially free of all other isomers). For example, the isomer may comprise at least 50% by weight of all 3-acetylamino-4-hydroxy-α-phenylethyl)aminomethyl benzyl alcohol present, preferably at least 75%, such as at least 90%, at least 95% or at least 99%.

As used herein, the term "pharmaceutically acceptable salt" refers to a salt prepared from a pharmaceutically acceptable, relatively non-toxic acid, including inorganic acids and organic acids. Suitable acids include acetic, benzenesulfonic, benzoic, camphorsulfonic, carbonic, citric, dihydrogenphosphoric, ethenesulfonic, fumaric, galactunoric, gluconic, glucuronic, glutamic, hydrobromic, hydrochloric, hydriodic, isobutyric, isethionic, lactic, maleic, malic, malonic, mandelic, methanesulfonic, monohydrogencarbonic, monohydrogenphosphoric, monohydrogensulfuric, mucic, nitric, pamoic, pantothenic, phosphoric, phthalic, propionic, suberic, succinic, sulfuric, tartaric, toluenesulfonic, including p-toluenesulfonic m-toluenesulfonic and o-toluenesulfonic acids, and the like (see, e.g., Berge et al., J. Pharm. Sci., 66:1-19 (1977); Stahl and Wermuth, Handbook of Pharmaceutical Salts, Wiley VCH, (2002)). Also included are salts of other relatively non-toxic compounds that possess acidic character, including amino acids, such as arginine and the like, and other compounds, such as aspirin, ibuprofen, saccharin, and the like. Acid addition salts can be obtained by contacting the neutral form of such compounds with a sufficient amount of the desired acid, either neat or in a suitable inert solvent. As solids, salts can exist in crystalline or amorphous modifications.

The compounds of the present invention may also be prepared in deuterated form, i.e., in which one or more hydrogen atoms, for example on the acetyl group, are replaced with deuterium.

It is also contemplated that the acetyl group in the compound of formula (I) may be replaced with a fluoroacetyl group (i.e. a group in which one, two or three of the acetyl hydrogen atoms is replaced with a fluorine atom). Such compounds may be prepared by a process analogous to that described herein for the preparation of the acetyl compound.

The acetamide isomer and its pharmaceutically acceptable salts can be prepared by a process, which comprises reacting a compound of general formula (II)

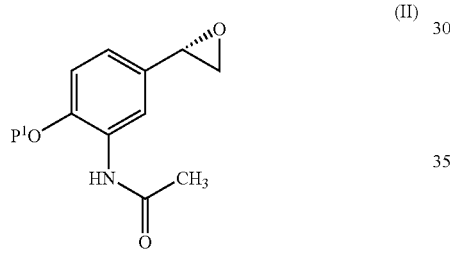

(II)

in which $P^1$ represents a hydrogen atom or a hydroxyl protecting group, with a compound of general formula (III)

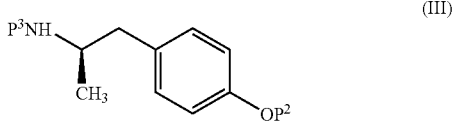

(III)

in which $P^2$ represents a hydrogen atom or a hydroxyl protecting group and $P^3$ represents a benzylic amine protecting group, to afford a compound of general formula (IV)

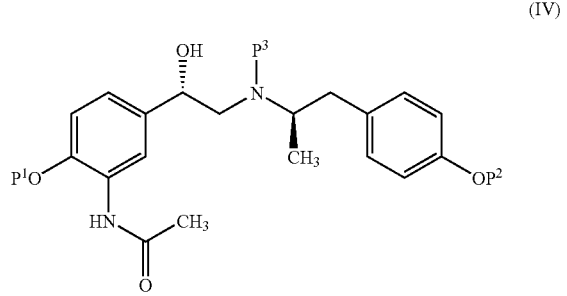

(IV)

or a salt thereof, followed by removing any protecting groups $P^1$, $P^2$ and $P^3$ and, if desired, forming a pharmaceutically acceptable acid addition salt.

The protecting groups may be any suitable protecting group, for example as described in Green et al., "Protective Groups in Organic Chemistry," (Wiley, $2^{nd}$ ed. 1991). Examples of hydroxyl protecting groups include aralkyl groups, such as benzyl, and trialkylsilyl groups, such as t-butyl-dimethylsilyl (TBDMS). Examples of a benzylic amine protecting group are benzyl groups optionally substituted on the benzene ring by one or more, for example 1, 2 or 3 optional substituents, for example selected from halo, (1-4C) alkyl and (1-4C)alkoxy; for example unsubstituted benzyl.

The reaction between the compounds of formula (II) and (III) is conveniently performed by melting the two compounds together, for example by heating in the range of from 110 to 130° C.

Any protecting groups represented by $P^1$, $P^2$ and $P^3$ may be removed using a conventional procedure. For example, a benzyl group can be removed by catalytic hydrogenation in the presence of palladium on carbon, and a trialkylsilyl group by treatment with tetrabutylammonium fluoride.

Compounds of formula (II) can be prepared by reacting a compound of formula (V)

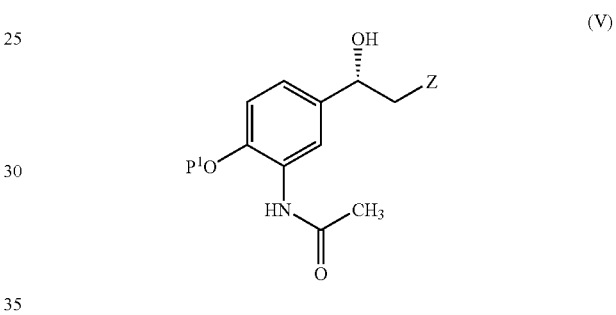

(V)

in which Z represents a leaving atom or group, such as a bromine atom, with a base, for example an alkali metal carbonate such as potassium carbonate.

Compounds of formula (V) can be prepared by stereoselective reduction of a compound of formula (VI)

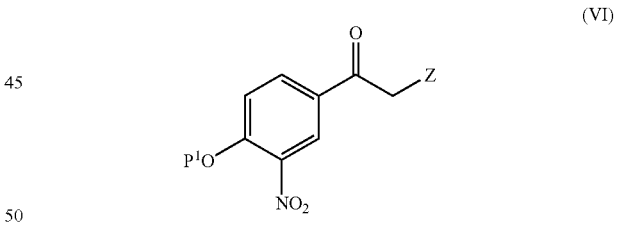

(VI)

using, for example, borane in the presence of a chiral auxiliary, such as (1S,2R)-1-amino-2-indanol, followed by reduction of the nitro group to an amino group and acetylation of the resultant amino group.

Compounds of general formula (III) can be prepared by reacting a compound of general formula (VII)

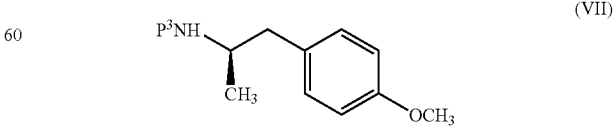

(VII)

with boron tribromide, to afford a compound of formula (VIII)

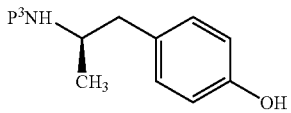

(VIII)

The hydroxyl group may then be protected, for example by reaction with a trialkylsilyl halide, such as t-butyldimethylsilyl chloride.

It will be appreciated that the percentage by weight comprised by the compound of formula (I) of all 3-acetylamino-4-hydroxy-α-phenylethyl)aminomethyl benzyl alcohol present in the final product of the process will depend upon the enantiomeric purity of the starting materials used and any enantiomeric purification steps taken, such as chiral liquid chromatography.

The intermediates of general formula (IV) are believed to be novel and are provided as a further aspect of the present invention.

According to another aspect, therefore, the present invention provides a pharmaceutical composition, which comprises a compound of formula (I) or a pharmaceutically acceptable salt thereof, as described herein, together with a pharmaceutically acceptable carrier.

The pharmaceutical composition according to the invention may be adapted for administration to patients by any convenient route, such as by oral, mucosal (e.g. nasal, sublingual, vaginal, buccal or rectal), parenteral or transdermal administration. It may be in the form of, for example, a solution, suspension, powder, tablet, aerosol formulation, lozenge, suppository, emulsion, hard or soft gelatin capsule or syrup. The compound of formula (I) may be dissolved in the carrier, diluted by the carrier or supported by the carrier. Thus the carrier may be a support for the compound of formula (I), such as a capsule, sachet, paper or other pharmaceutical container.

In one embodiment, the pharmaceutical composition is an aqueous solution adapted for administration using a nebuliser. The aqueous formulation may be isotonic and buffered at an optimal pH for stability. The aqueous formulation for nebulization could also be a suspension of nanoparticles or a micronized suspension of free base or an insoluble salt or a cyclodextrin adduct.

In another embodiment, the pharmaceutical composition is an aerosol formulation adapted for administration using a metered dose inhaler, the aerosol formulation comprising the acetamide isomer in crystalline form and a propellant or in solution with an appropriate propellant, combination of propellants or combination of propellant(s) and an acceptable co-solvent or other solubilizing agent.

The propellant may be any suitable propellant used in aerosol formulations, for example, a hydrofluoroalkane (HFA), such as 1,1,1,2-tetrafluoroethane (HFA134) or 1,1,1,2,3,3,3-heptafluoropropane (HFA227) or a combination of propellants. HFA134 is preferred. The propellant may comprise at least 90% by weight of the aerosol formulation, which may also include, inter alia, inert gases to aide in aerosol formation.

The aerosol formulation may further comprise a surfactant. The surfactant serves to stabilize and disperse the acetamide isomer in a suspension, and may also serve as a valve lubricant in the metered dose inhaler. It may be any suitable surfactant used in aerosol formulations. Examples of surfactants used in aerosol formulations are described in U.S. Pat. No. 5,225,183, which is hereby incorporated by reference. A preferred surfactant is oleic acid. The surfactant, when present, may generally be present in an amount of from 1:100 to 1:10 surfactant:acetamide isomer, preferably about 1:20.

The aerosol formulation may further comprise a co-solvent. A function of the co-solvent in the aerosol formulation is to facilitate dissolution of the surfactant, which may have poor solubility in the propellant. It may be any suitable carrier used in aerosol formulations. A co-solvent such as glycerol or ethanol may be used. A preferred co-solvent is ethanol, especially dehydrated ethanol. The content of ethanol may conveniently be up to 30% by weight of the aerosol formulation, such as from 2 to 6%.

Metered dose inhalers typically comprise a canister containing an aerosol formulation, a metering valve, a valve stem and an actuator which accepts the valve stem. In use, a patient depresses the canister into the actuator and inhales, causing a dose of the formulation to be administered and taken into the patient's lungs.

According to a further aspect, therefore, the present invention provides a metered dose inhaler comprising a canister containing an aerosol formulation as described herein, a metering valve and an actuator.

Preferably the interior surface of the canister is coated, for example with a protective polymer, or otherwise treated to minimize chemical or physical interaction between the formulation and the canister. The inhaler preferably has an aperture with a diameter in the range of from 0.2 to 0.60 mm.

In yet another embodiment, the pharmaceutical composition is in the form of a dry powder suitable for inhalation or insufflation. The composition may comprise acetamide isomer crystals alone (e.g. having a mass median aerodynamic diameter of from 1 to 10 microns, preferably from 2 to 7 microns), or acetamide isomer blended, co-precipitated, co-crystallized or spray dried together with a suitable pharmaceutically acceptable carrier or carriers. Suitable pharmaceutically acceptable carriers include, without limitation, solvates of one or more natural or synthetic carbohydrates, such as a monosaccharides, disaccharides, trisaccharides, oligosaccharides, polysaccharides, polyols, amino acids and proteins, and/or in the form of their pharmaceutically acceptable esters, acetals, or salts (where such derivatives exist). The carrier is preferably lactose, more preferably lactose monohydrate. The dry powder composition may be presented in unit dosage form in, for example, capsules or cartridges of e.g. gelatin, or blister packs from which the powder may be administered with the aid of an inhaler or insufflator. The dry powder composition may be presented in multi dose form metered with the aid of an inhaler or insufflator, or pre-metered into discrete doses within the device for serial administrations.

Conveniently, dry powder formulations are administered using multidose dry powder inhalers.

The present invention therefore also provides a multidose dry powder inhaler, comprising a dry powder reservoir containing a dry powder aerosol formulation of acetamide isomer as described hereinabove, and a metering chamber.

The compound of formula (I) according to the present invention may be co-administered with one of more other active ingredients, for example selected from steroids, such as beclomethasone, triamcinolone, funisolide, mometasone, budesonide or fluticasone, muscarinic receptor antagonists, such as ipratropium, tiatropium, or glycopyrrolate. Accordingly, in one embodiment, the pharmaceutical composition in accordance with the present invention may further comprise a steroid and/or a muscarinic receptor antagonist and/or a controller agent or bronchodilator with a novel mechanism.

In another embodiment, the pharmaceutical composition in accordance with the present invention may further comprise anti-inflammatory agents such as inhibitors of tumor necrosis factor alpha (TNFα), dipeptidyl peptidase IV, and antibodies to pro-inflammatory interleukins such as IL4 and IL13.

In another embodiment, the pharmaceutical composition in accordance with the present invention may further comprise mucolytic agents such as cromoglycate, acetylcysteine, arginine, or 2-mercaptoethanesulphonate.

According to another aspect, the present invention provides a method of treating bronchoconstrictive disease, which comprises administering to a patient in need of treatment an effective amount of a compound of formula (I) or a pharmaceutically acceptable salt thereof.

The bronchoconstrictive disease may be, for example, chronic obstructive pulmonary disease (such as emphysema or bronchitis), cystic fibrosis, or asthma.

The patient may be a human or a non-human mammal, such as a dog, cat, horse, cow, sheep or pig. Preferably, the patient is a human.

The amount of compound administered will depend upon many factors, such as the species, weight and age of the patient, and the severity of the condition to be treated. For example, a dose administered to a human may contain from 75 to 5,000 μg of the acetamide isomer (calculated as the free base). The dose may be administered, for example, once or twice per day.

According to another aspect, the present invention provides a compound of formula (I) or a pharmaceutically acceptable salt thereof, for use in therapy.

According to yet another aspect, the present invention provides the use of a compound of formula (I) or a pharmaceutically acceptable salt thereof in the manufacture of a medicament for the treatment of chronic obstructive pulmonary disease.

According to a still further aspect, the present invention provides a pharmaceutical composition comprising a compound of formula (I) or a pharmaceutically acceptable salt thereof and a pharmaceutically acceptable carrier for the treatment of chronic obstructive pulmonary disease, or for use as a bronchodilator.

Although the foregoing invention has been described in some detail for purposes of illustration, it will be readily apparent to one skilled in the art that changes and modifications may be made without departing from the scope of the invention described herein.

EXAMPLES

The following Examples illustrate the invention.

THF refers to tetrahydrofuran, EtOAc refers to ethyl acetate and Et$_2$O refers to diethyl ether.

Example 1

N-[2-hydroxy-5-[(1S)-1-hydroxy-2-[[(1R)-2-(4-hydroxyphenyl)-1-methylethyl]amino]ethyl]phenyl]acetamide Step A) (1S)-1-(3-nitro-4-benzyloxyphenyl)-2-bromoethan-1-ol

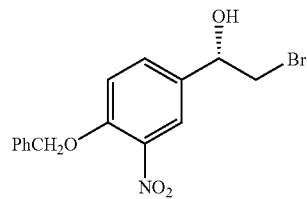

A cold (5° C.) solution of (1S,2R)-1-amino-2-indanol (400 mg, 2.68 mmol) in THF (160 mL) was added dropwise to a cold (0° C.) solution of borane-diethylaniline complex (7.0 g, 43 mmol) in THF (20 mL). After complete addition, the resulting solution was stirred at (0° C.) for 30 min then 2-bromo-4'-benzyloxy-3'-nitroacetophenone (20.0 g, 57.1 mmol) was added in three portions over a 30 min period. The resulting solution was stirred at <5° C. for 1 h, quenched by dropwise addition of acetone (17 mL) then allowed to warm to ambient temperature overnight. The reaction mixture was concentrated in vacuo to a residue, which was dissolved in toluene (100 mL) and washed in succession with 10% H$_2$SO$_4$ (2×45 mL), H$_2$O (2×45 mL) and sat. brine (1×40 mL). The organic layer was dried over MgSO$_4$, clarified then concentrated in vacuo to a volume of ~40 mL. Heptane (45 mL) was slowly added to give a thick slurry. The solid was collected on a filter and washed with heptane (2×5 mL). This material was dissolved in warm toluene (~50 mL), the solution was clarified then diluted with heptane (50 mL). The resulting mixture was stirred for 30 min, the solids were collected, washed with heptane (2×5 mL) then dried to constant weight in vacuo to give 18.9 g (94.0%) of the title compound.

Step B) (1S)-1-(3-amino-4-benzyloxyphenyl)-2-bromoethan-1-ol

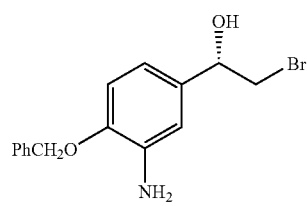

A solution of the product of step A) (18.7 g, 53.1 mmol) in toluene (40 mL) and THF (40 mL) was added to a Parr shaker bottle containing Pt$_2$O (370 mg). This mixture was shaken under H$_2$ (50 psi, 344.74 kpa) until the reaction was complete (18 h). The catalyst was removed by filtration, and the filtrate was concentrated to an oil. Column chromatography (1 kg silica gel packed in and eluted with CH$_2$Cl$_2$/MeOH, 19:1) gave 11.9 g (69.6%) of the title compound.

Step C) (1S)-1-(3-acetamido-4-benzyloxyphenyl)-2-bromoethan-1-ol

A solution of the product in step B (10.0 g, 31.0 mmol) in pyridine (100 mL) was stirred at ambient temperature for 10 min. Acetic anhydride (3.16 g, 30.9 mmol) was added, and the reaction mixture was stirred at ambient temperature for 30 min then at 40° C. for 4.5 h. The reaction mixture was cooled to ambient temperature then concentrated in vacuo to a residue. This material was partitioned between $CH_2Cl_2$ (120 mL) and 10% aq HCl (50 mL). The aqueous layer was extracted with $CH_2Cl_2$ (50 mL). The combined organic layers were washed in succession with $H_2O$ (1×100 mL) and brine (1×100 mL), dried over $MgSO_4$, clarified then concentrated in vacuo to a thick slurry. After dilution with hexanes (60 mL), the solid was collected on a filter, washed with hexanes (2×20 mL) then dried to constant weight in vacuo to give 9.4 g (83%) of material as a white solid.

Step D) (1S)-1-(3-acetamido-4-benzyloxyphenyl)epoxyethane

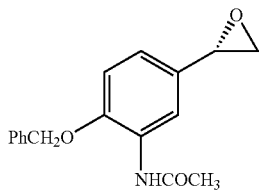

A solution of the product in step C (2.5 g, 6.9 mmol) in MeOH (15 mL) and THF (15 mL) was treated with $K_2CO_3$ (1.3 g, 9.4 mmol), and the resulting mixture was stirred at ambient temperature for 2.5 h. The mixture was concentrated in vacuo to a residue, which was partitioned between $H_2O$ (50 mL) and EtOAc (50 mL). The aqueous layer was extracted with EtOAc (50 mL). The combined organic extracts were washed with $H_2O$ (50 mL treated with a pinch of $K_2CO_3$ to make it basic), dried over $Na_2SO_4$, clarified then concentrated in vacuo to a residue that was dried to constant weight in vacuo to give 1.84 g (94%). This material was used in the next reaction step without further purification.

Step E) [(1R)—N-Benzyl-2-(4-hydroxyphenyl)-1-methylethyl]-amine

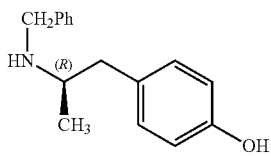

To a solution of [(1R)—N-Benzyl-2-(4-methoxyphenyl)-1-methylethyl]amine (5.30 g, 20.8 mmol) in $CH_2Cl_2$ (25 mL) was added a solution of $BBr_3$ in $CH_2Cl_2$ (25.0 mL, 1.0M, 25.0 mmol) slowly over 0.5 h. After the addition, the mixture was stirred at ambient temperature for 22 h. Water (125 mL) was added, followed by the addition of 2.5M aq. NaOH (15 mL) to pH 6. The mixture was extracted with EtOAc (4×200 mL), and the organic layer was dried ($Na_2SO_4$) and concentrated. The residue (3.9 g) was triturated with $CH_2Cl_2$ (120 mL) and then concentrated to dryness to give the title compound (3.8 g, 76%).

Step F) [(1R)—N-Benzyl-2-(4-t-butyldimethylsilyloxyphenyl)-1-methylethyl]amine

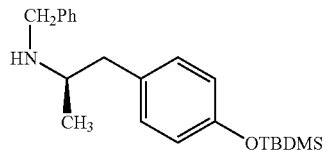

A solution of the product of step E) (3.20 g, 13.3 mmol), tert-butyldimethylsilyl chloride (3.59 g, 23.8 mmol), and imidazole (2.86 g, 42.0 mmol) in DMF (30.0 mL) was stirred at ambient temperature for 18 h. The mixture was concentrated to dryness, and the residue was partitioned between EtOAc (200 mL) and sat. aq. $NaHCO_3$ (200 mL). The aqueous layer was separated and again extracted with EtOAc (100 mL). The combined organic layer was washed with brine (100 mL), dried with $Na_2SO_4$, filtered and concentrated to give an oil. The oil was chromatographed on silica gel (100 g, eluted with 1:1 EtOAc:hexanes) to give the title compound (4.0 g, 85%) as a tan oil.

Step G) N-[2-Benzyloxy-5-[(1S)-1S-hydroxy-2-[N'-benzyl-[(1R)-2-(4-t-butyldimethylsilyloxyphenyl)-1-methylethyl]amino]ethyl]-phenyl]acetamide

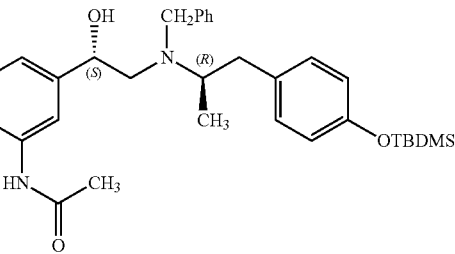

A mixture of the products of Step D) (1.75 g, 6.18 mmol) and F) (2.20 g, 6.19 mmol) was heated slowly to 110° C. to give a complete solution. The reaction solution was heated at 120° C. for 20 h. TLC (EtOAc/hexanes, 1:1) showed an estimated 5% of starting material remaining. Heating was continued at 120° C. for 5 h then the solution was cooled to ambient temperature and chromatographed over a column of silica gel (200 g) packed in and eluted with hexanes/EtOAc (2:1). Fractions containing purified material were combined, clarified then concentrated in vacuo to afford the title compound as a yellow oil, 3.4 g (86%).

Step H) N-[2-Benzyloxy-5-[(1S)-1-hydroxy-2-[N'-benzyl-[(1R)-2-(4-t-hydroxyphenyl)-1-methylethyl]amino]ethyl]phenyl]acetamide

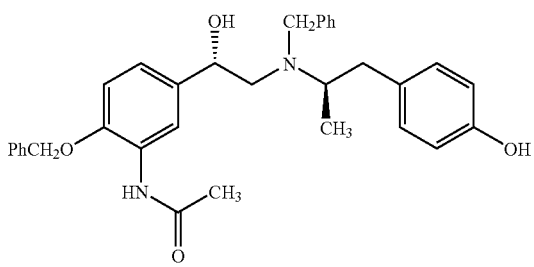

To a stirred solution of the product of Step G) (2.20 g, 3.44 mmol) in THF (22 mL) at 5-10° C., a solution of tetra-n-butylammonium fluoride in THF (1.0 M, 4.50 mL, 4.50 mmol) was added. The reaction mixture was stirred at ambient temperature for 1 h (Note 2), and TLC (1:1 EtOAc/hexanes) showed complete consumption of 8. The reaction mixture was diluted with EtOAc (300 mL) and washed with deionized $H_2O$ (4×200 mL), then dried ($MgSO_4$), filtered, and concentrated to give crude 9 (2.3 g). The crude material was purified on a column of flash silica gel (82 g, 2.7×35 cm), packed in and eluted with 1:1 EtOAc/hexanes. Fractions containing the purified product were combined and concentrated to give a colorless, viscous oil. The oil was coevaporated with $Et_2O$ (3×25 mL) to give the title compound (919 mg, 51%) as a white solid.

Step I) N-[2-hydroxy-5-[(1S)-1-hydroxy-2-[[(1R)-2-(4-hydroxyphenyl)-1-methylethyl]amino]ethyl]phenyl]acetamide

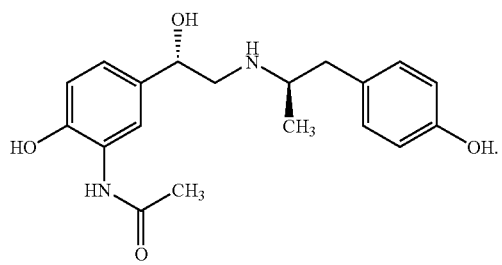 [SMILES: CC(=O)Nc1cc([C@H](O)CN[C@H](C)Cc2ccc(O)cc2)ccc1O]

A mixture of the product of step H) (900 mg, 1.72 mmol), palladium on carbon (500 mg of 10 wt % Pd) and EtOH (45 mL) was shaken under $H_2$ (50 psi, 344.74 kpa) for 22 h. The mixture was clarified then concentrated in vacuo to an oily residue. The residue was co-evaporated with EtOAc (100 mL) and EtOAc/$CH_2Cl_2$ (1:1, 100 mL) to give a white solid (536 mg). TLC (4:1 $CH_2Cl_2$/MeOH) of the solid showed some upper Rf impurities. The solid was dissolved in $CH_2Cl_2$ (20 mL)/MeOH (1 mL), then concentrated in the cold to ~10 mL. Hexanes (~20 mL) were added, and the mixture was again concentrated in the cold to give a suspension. A mixture of $Et_2O$ (5 mL), EtOAc (5 mL) and hexanes (5 mL) was added, and the mixture was concentrated to give a slurry. This slurry was diluted with hexanes (25 mL), and the suspension was stirred vigorously for 0.5 h at room temperature. The solid was collected and washed with hexanes (25 mL) to give the title compound (318 mg, 54%); m.p. 97-100° C., with previous softening (uncorrected). MS m/z: [M+H$^+$]345.1. $^1$H NMR spectrum consistent with the assigned structure.

$\beta_1$ and $\beta_2$ Radioligand Binding Assays

The affinity of a test compound for adrenergic $\beta_1$ and $\beta_2$ receptors is investigated by evaluating the ability of the compound to displace specific binding of [$^{125}$I]-cyanopidolol or [$^3$H]-CGP-12177 at human recombinant $\beta_1$ and $\beta_2$ receptors, respectively (expressed in CHO cells). The $IC_{50}$ is defined as the concentration that inhibits 50% of specific binding of the radioligand. The $K_i$ is calculated from the $IC_{50}$ and the known $K_D$ of the radioligand (Cheng and Prusoff's equation).

In this test, the compound of Example 1 was found to afford a $K_i$ of >20 μM with only 30% inhibition of specific binding at a concentration of 20 μM for the $\beta_1$ receptor and 2.21 μM for the $\beta_2$ receptor. The $\beta_1/\beta_2$ binding ratio was found to be >9.

By way of comparison, the values found for arformoterol and the (S,R) isomer of formoterol were 0.155 μM ($\beta_1$), 0.004 μM ($\beta_2$) and 41($\beta_1/\beta_2$), and 2.50 μM ($\beta_1$), 0.075 μM ($\beta_2$) and 33($\beta_1/\beta_2$), respectively.

Intrinsic Activity Assessment ($\beta_2$)

The intrinsic activity of a test compound is assessed by evaluating its ability to increase cAMP production from human recombinant $\beta_2$ receptors expressed in CHO cells. Data are expressed as % response relative to a procaterol-induced cAMP increase.

The compound of Example 1 was found to have an intrinsic activity of 71%.

By way of comparison, arformoterol and (S,R)-formoterol were found to have intrinsic activities of 98% and 91% respectively.

$\beta_1$ and $\beta_2$ Adrenergic Activity (Functional)

Functional agonism at adrenergic $\beta_1$ receptors is demonstrated by a positive chronotropic effect in isolated right atria from Dunkin Hartley Guinea pigs. The concentration that gives 50% maximal effect is the $EC_{50}$.

Functional agonism at adrenergic $\beta_2$ receptors is demonstrated by relaxation of the spontaneous tone of isolated trachea from Dunkin Hartley Guinea pigs. The concentration that gives 50% maximal effect is the $EC_{50}$.

In these tests, an $EC_{50}$ could not be determined for the compound of Example 1 for the $\beta_1$ functional assay as only a 32% increase in heart rate was seen at a concentration of 30 μM. However, the compound of Example 1 was found to have an $EC_{50}$ of 120 nM for the $\beta_2$ receptor. The $\beta_1/\beta_2$ functional ratio was found to be >250.

By way of comparison, the values found for arformoterol were 3 nM ($\beta_1$), 0.041 nM ($\beta_2$) and 75.

Stability in Aqueous Buffered Solutions

Solution Preparations: For each test compound, the following solutions are prepared.

Solution A is prepared from ~30 mg of the test compound in 150 mL of 0.005 M citrate buffer, pH 5.0 (~0.2 mg/mL).

Solution B is prepared as follows: approximately 30 mL aliquot of Solution A is transferred to a separated container and the pH of the solution is adjusted to pH 3.0 with 1 N HCl (~0.2 mL).

Solution C is prepared as follows: approximately 30 mL aliquot of Solution A is transferred to a separated container and the pH of the solution is adjusted to pH ~8.0 with 1 N NaOH (~0.2 mL).

Note: Because the volume of 1 N HCl or 1 N NaOH used for adjusting pH was negligible, the concentration of test compound in Solutions A, B and C were the same.

Storage Scheme

As soon as the above solutions were prepared, aliquots of each solution were transferred into 11 vials, of which 9 vials are stored at −20° C., and one each is stored at 30° C. and 40° C., respectively.

At each interval listed below, two vials are removed from −20° C. storage, and stored at 30° C. and 40° C., respectively.

The corresponding weeks under the storage condition (30° C. or 40° C.) are shown in the table below.

|  | Week of Vial Removal | | | | | |
|---|---|---|---|---|---|---|
|  | 0 | 4 | 8 | 10 | 11 | 12 |
| Weeks Under Storage Condition (30° C. or 40° C.) | 12 | 8 | 4 | 2 | 1 | 0 |

On Week 12, the last vial stored at −20° C. is removed and warmed up to the room temperature, which is the Day 0 Solution.

Sample Analysis: On Week 12, all solutions are assayed by an HPLC method using the Day 0 Solution at pH 5 as a standard solution. The test compounds were assayed by HPLC with UV detection (refer to Table 1 for method conditions).

TABLE 1

| HPLC Method Conditions | |
|---|---|
| Parameter | Method Detail |
| Column | Zorbax SB C8 |
|  | 150 × 4.6 mm |
| Mobile Phase A | 0.027 M phosphate buffer |
|  | (pH 3.2)/ACN, 95/5, v/v |
| Mobile Phase B | 0.027 M phosphate buffer |
|  | (pH 3.2)/ACN, 30/70, v/v |
| Column Temp | Ambient |
| Sampler Temp | 5° C. |
| Injection Volume | 5 μL |
| Flow Rate | 1.0 mL/min |
| Wavelength | PDA 200-350 nm |
| Run Time | 55 min |

| | Time (min) | % A | % B |
|---|---|---|---|
| Gradient Table | 0 | 100 | 0 |
|  | 10 | 90 | 10 |
|  | 25 | 80 | 20 |
|  | 35 | 65 | 35 |
|  | 47 | 0 | 100 |
|  | 50 | 100 | 0 |
|  | 55 | 100 | 0 |

TABLE 2

Stability of Compound of Example 1 in Aqueous Solution
(% of Initial Concentration (0.20113 mg/mL) in pH 5.0 Citrate Buffer)

| | Condition | | | | | |
|---|---|---|---|---|---|---|
| | pH 3.0 | | pH 5.0 | | ~pH 8 | |
| Time(wk) | 30° C. | 40° C. | 30° C. | 40° C. | 30° C. | 40° C. |
| 0 | 99.46 | 99.46 | 100.25 | 100.25 | 100.38 | 100.38 |
| 1 | 100.03 | 99.89 | 101.22 | 102.00 | 99.64 | 97.44 |
| 2 | 99.84 | 100.11 | 101.07 | 102.73 | 99.60 | 93.75 |
| 4 | 101.41 | 99.54 | 112.52* | 102.94 | 96.62 | 86.72 |
| 8 | 100.33 | 99.18 | 107.12 | 122.32* | 26.79* | 72.25 |
| 12 | 100.29 | 97.17 | 107.75 | 112.61* | 89.93 | 61.36 |

*These results were out of trend, but the cause was unknown. The high results at pH 5 might be due to evaporation at elevated temperature during storage.

CONCLUSION

At pH 3 or 5, the compound of Example 1 was found to be very stable for at least 12 weeks when stored at 30° C.

What is claimed is:

1. A compound of formula (I)

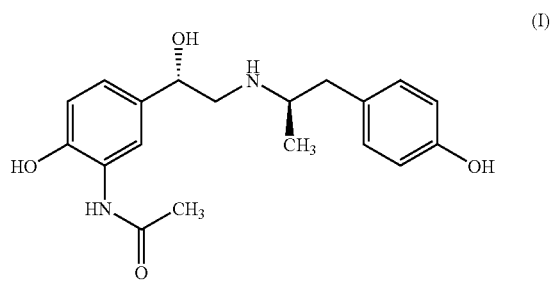 [SMILES: CC(=O)Nc1cc([C@H](O)CN[C@H](C)Cc2ccc(O)cc2)ccc1O]

or a pharmaceutically acceptable salt thereof.

2. A mixture of isomers of N-[2-hydroxy-5-[1-hydroxy-2-[[(2-(4-hydroxyphenyl)-1-methylethyl]amino]ethyl]-phenyl]acetamide, wherein the mixture comprises at least 90% by weight of the isomer

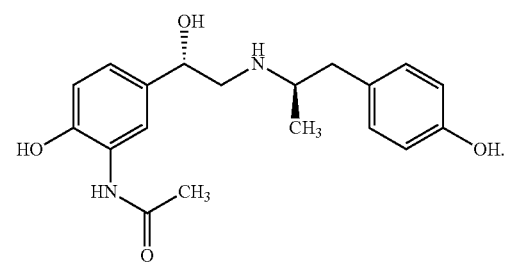 [SMILES: CC(=O)Nc1cc([C@H](O)CN[C@H](C)Cc2ccc(O)cc2)ccc1O]

3. A compound of general formula (IV)

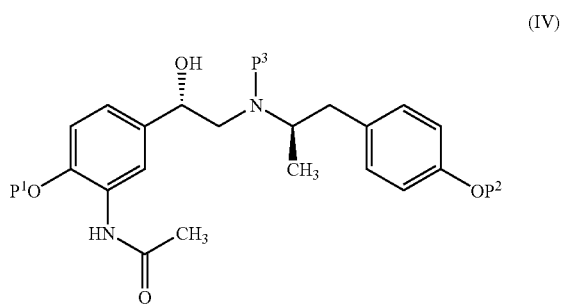

or a salt thereof, in which $P^1$ and $P^2$ each represents a hydrogen atom or a hydroxyl protecting group, and $P^3$ represents a hydrogen atom or a benzylic amine protecting group, provided that at least one of $P^2$ and $P^3$ represents a protecting group.

4. A pharmaceutical composition, which comprises a compound as claimed in claim 1 or claim 2 and a pharmaceutically acceptable carrier.

5. A pharmaceutical composition as claimed in claim 4, which further comprises a steroid.

6. A pharmaceutical composition as claimed in claim 5, in which the steroid is beclomethasone, triamcinolone, funisolide, mometasone, budesonide or fluticasone.

7. A pharmaceutical composition as claimed in any one of claims 4 to 6, which further comprises a muscarinic receptor antagonist.

8. A pharmaceutical composition as claimed in claim 7, in which the muscarinic receptor antagonist is ipratropium or tiatropium.

9. A pharmaceutical composition as claimed in any one of claims 4 to 8 which further comprises an anticholinergic.

10. A pharmaceutical composition as claimed in claim 9, in which the anticholinergic is glycopyrralate.

11. A pharmaceutical composition as claimed in any one of claims 4 to 10 which further comprises a mucolytic.

12. A pharmaceutical composition as claimed in claim 11, in which the mucolytic is cromoglycate, acetylcysteine, arginine, or 2-mercaptoethanesulphonate.

13. A pharmaceutical composition as claimed in any one of claims 4 to 12 which further comprises an anti-inflammatory agent.

14. A pharmaceutical composition as claimed in claim 13, in which the anti-inflammatory agent is an inhibitor of tumor necrosis factor alpha (TNFα) or dipeptidyl peptidase IV, and/or antibodies to pro-inflammatory interleukins such as IL4 and IL13.

15. A method for treating bronchoconstriction associated with a reversible obstructive airways disease, which comprises administering to a patient in need of treatment, an effective amount of a compound as claimed in claim 1.

* * * * *

UNITED STATES PATENT AND TRADEMARK OFFICE
CERTIFICATE OF CORRECTION

PATENT NO.        : 8,501,994 B2
APPLICATION NO.   : 12/196520
DATED             : August 6, 2013
INVENTOR(S)       : Craig R. Abolin et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 928 days.

Signed and Sealed this
Seventh Day of July, 2015

Michelle K. Lee
*Director of the United States Patent and Trademark Office*